United States Patent
Mathies et al.

(10) Patent No.: US 6,623,613 B1
(45) Date of Patent: Sep. 23, 2003

(54) MICROFABRICATED LIQUID SAMPLE LOADING SYSTEM

(75) Inventors: Richard A. Mathies, Moraga, CA (US); Charles A. Emrich, Berkeley, CA (US); Peter C. Simpson, Mountain View, CA (US)

(73) Assignee: The Regents of the University of California, Oakland, CA (US)

( * ) Notice: Subject to any disclaimer, the term of this patent is extended or adjusted under 35 U.S.C. 154(b) by 265 days.

(21) Appl. No.: 09/678,351

(22) Filed: Oct. 2, 2000

Related U.S. Application Data

(60) Provisional application No. 60/157,299, filed on Oct. 1, 1999.

(51) Int. Cl.[7] .................. B01D 57/02; B01D 59/42; B01D 59/50; B01D 61/42; B01D 61/58; C02F 1/469; C07K 1/26; C08F 2/58
(52) U.S. Cl. ................. 204/453; 204/450; 204/600
(58) Field of Search ................. 204/453, 600, 204/450

(56) References Cited

U.S. PATENT DOCUMENTS

| | | | |
|---|---|---|---|
| 5,681,484 A | * 10/1997 | Zanzucchi et al. | ............ 216/2 |
| 6,100,535 A | 8/2000 | Mathies et al. | |
| 6,103,199 A | * 8/2000 | Bjornson et al. | ............ 204/450 |
| 6,143,152 A | * 11/2000 | Simpson et al. | ............ 204/451 |
| 6,416,642 B1 | * 7/2002 | Alajoki et al. | ............ 204/451 |
| 6,451,188 B1 | * 9/2002 | Sundberg et al. | ............ 204/453 |

FOREIGN PATENT DOCUMENTS

| WO | WO 97/34138 | 9/1997 |
|---|---|---|
| WO | WO 99/15888 | 4/1999 |
| WO | WO 99/19717 | 4/1999 |
| WO | WO 99/24827 | 5/1999 |

* cited by examiner

Primary Examiner—Mark L. Bell
Assistant Examiner—Jennine Brown
(74) Attorney, Agent, or Firm—Townsend and Townsend and Crew LLP

(57) ABSTRACT

A microfabricated liquid sample loading system comprising a first plate having an array of microfabricated holes passing therethrough; a second plate positioned against the first plate, the second plate having an array of microfabricated holes passing therethrough; and a plurality of microfabricated channels disposed on a surface of at least one of the first or second plates, the microfabricated channels connecting the array of microfabricated holes in the first plate with the array of microfabricated holes in the second plate.

41 Claims, 11 Drawing Sheets

FIG. 7A
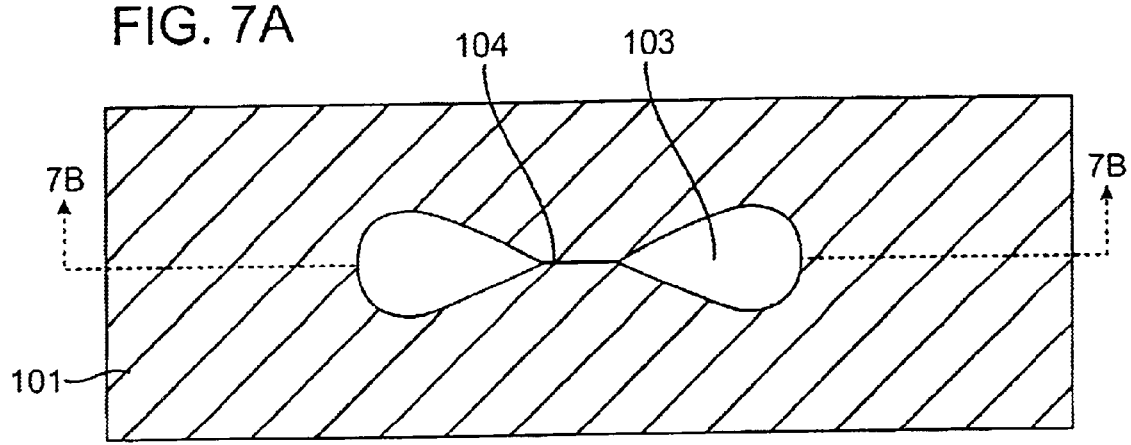
FIG. 7B
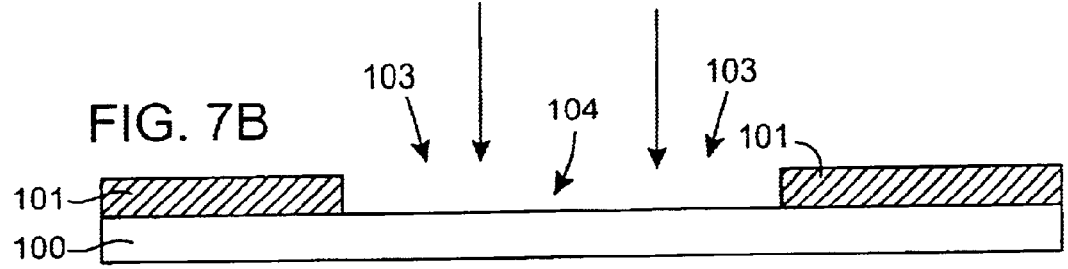
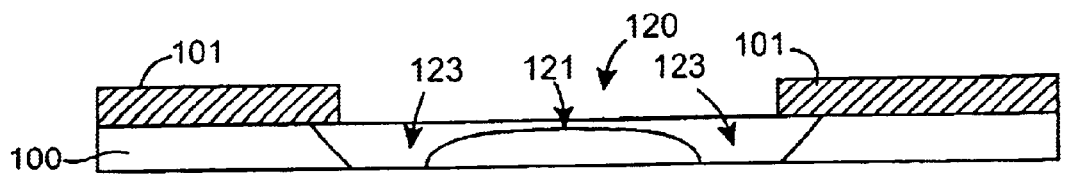
FIG. 7C

MICROFABRICATED LIQUID SAMPLE LOADING SYSTEM

CROSS-REFERENCES TO RELATED APPLICATIONS

This application is a continuation of and claims the benefit of priority from provisional application No. 60/157,229 filed on Oct. 1, 1999, the full disclosure of which is incorporated herein by reference.

TECHNICAL FIELD

The present invention relates in general to microfluidic systems and to electrophoretic separation analysis systems and to fluid sample loading systems.

BACKGROUND OF THE INVENTION

Microchip electrophoresis separation technology has developed separation and detection systems which take only minutes to analyze many samples in parallel. Such rapid high density microcapilary separation and detection array systems have been microfabricated, for example, on glass microplates.

High throughput separation and detection systems require not only high speed separation and data collection, but they also require fast and efficient systems for introducing small amounts of samples and reagents into the analysis system. A problem with existing systems is that as the newer microplate technologies require considerably less time to perform parallel separation and detection, the actual time taken to load such arrays is becoming the time bottleneck for system operation.

Current methods of loading such arrays, such as using serial or parallel pipette loaders are time consuming, and only serial loading is well suited to loading non-orthogonal arrays of wells. Although robotic fluid loading systems are useful, they are complex, expensive, and generally not well adapted to load non-orthogonal arrays. Other current loading systems such as systems using long flexible glass capillaries suffer from the disadvantage of clogging very easily, and problems of achieving uniform transfer rates.

SUMMARY OF THE INVENTION

In one preferred aspect, the present invention provides a system adapted to simultaneously transfer a plurality of small volumes of liquid samples from a first well geometry to a second well geometry. In preferred aspects, the present invention can be used to transfer small volumes of liquid samples from an orthogonal array format of sample wells to another array format using microfluidic channels in a layered substrate structure.

In optional preferred aspects, the array format into which the samples are transferred may comprise wells disposed around the outer perimeter of a circular microfabricated plate wherein the wells are connected to a radial array of separation channels in an electrophoretic separation microchannel system. Such a radial array of separation channels offers advantages because they are easily laid out, and they can be scanned by a novel confocal radial fluorescence detector, as disclosed in U.S. Pat. No. 6,100,535, incorporated herein in its entirety for all purposes.

An advantage of the present system is that a plurality of fluid samples can be transferred simultaneously from a first sample well format to a second sample well format, providing a fast system for loading a plurality of fluid samples into an analysis system simultaneously. A second advantage of the present system is that the various fluid samples can be loaded into the various wells in the receiving microplate in precisely metered volumes at precisely the same rate and at precisely the same time. This is particularly advantageous when loading a plurality of different samples into discrete electrophoretic separation channels such that the samples can then all be electrophoretically separated at the same time. This in turn permits multiplexing of various anode, cathode or waste reservoirs in the separation microplate. Multiplexing of the various anode, cathode or waste reservoirs in the separation microplate advantageously reduces the number of reservoirs which need to be formed on the surface of the separation microplate.

In preferred aspects, the analysis system into which the samples are simultaneously loaded comprises a microcapillary electrophoretic separation system, which may optionally comprise a plurality of microchannels etched onto a top surface of a micromachined plate or wafer. It is to be understood, however, that the present invention is directed to simultaneously loading samples into any array of wells in any analysis or detection system. As such, sample wells in systems other than microcapillary electrophoretic separation systems may also be loaded by the present invention.

In optional preferred aspects, the "layered substrate structure" of the present invention comprises two or more wafers placed one on top of the other. These wafers may be made of glass, silicon or plastics, or other suitable materials.

In preferred aspects of the invention, the small volumes of liquid samples transferred or loaded by the present invention comprise fluid samples in the microliter to sub-microliter range.

Advantageously, the present system can be fabricated with excellent control of exact device geometry, thereby providing microfluidic channels having very small lengths and volumes such that only a very small sample volume is required in these microfluidic channels. An advantage of the present invention is that, due to the small dimensions of the system, the potential for sample absorption into the walls of the microchannels is minimized, as is the potential for sample or reagent volume being used up in filling the microchannels of the present system.

A further advantage of the present invention is that a plurality of the present systems can be made by batch processing, whereby many wafer plates are made in parallel. This makes wafer plate stacks easily replaceable in the case of a clog or failure, and also allows for the production of multiple designs. Moreover, it is easy to fabricate a variety of different transfer devices designed for loading different array formats in accordance with the present invention.

A further advantage of the present invention is that its novel manifold design permits it to accept various different sample loading systems having different designs of channels thereon, further increasing system flexibility.

BRIEF DESCRIPTION OF THE DRAWINGS

FIG. 7A is top plan view of a plate and photoresist prior to differential depth etching through the plate.

FIG. 7B is a sectional view taken along line 7B-7B through the plate and photoresist prior to differential depth etching.

FIG. 7C is a sectional view taken along line 7B-7B through the plate and photoresist after differential depth etching.

DESCRIPTION OF THE SPECIFIC EMBODIMENTS

The present invention provides methods and apparatus to simultaneously transport a plurality of fluid samples from one array of sample wells having a first well layout to another array of sample wells having a second well layout.

Figure 1:
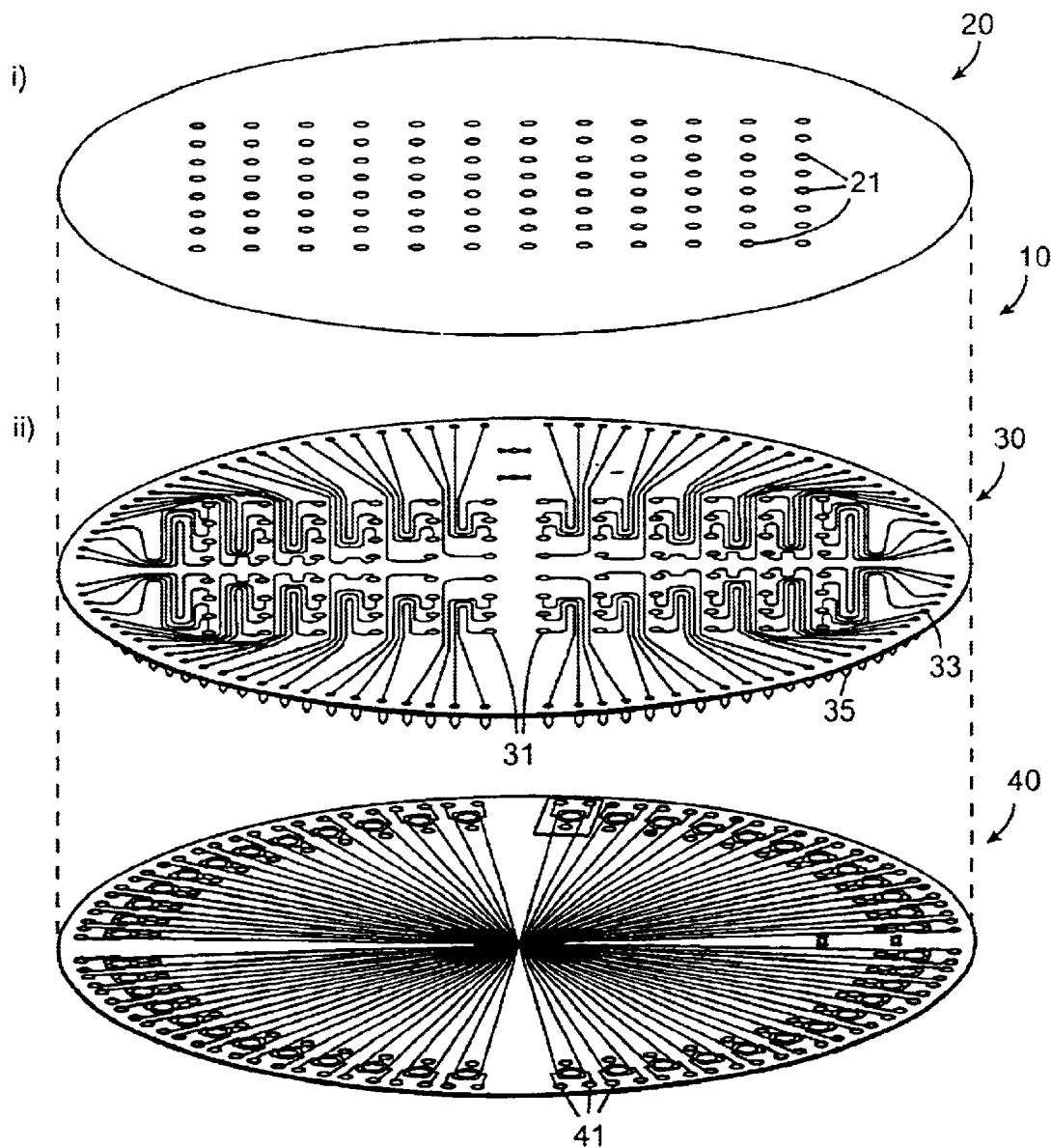
FIG. 1 is an exploded perspective view of the present two plate system, as positioned over a receiving radial channel microcapillary electrophoresis analysis microplate.
Figure 2:
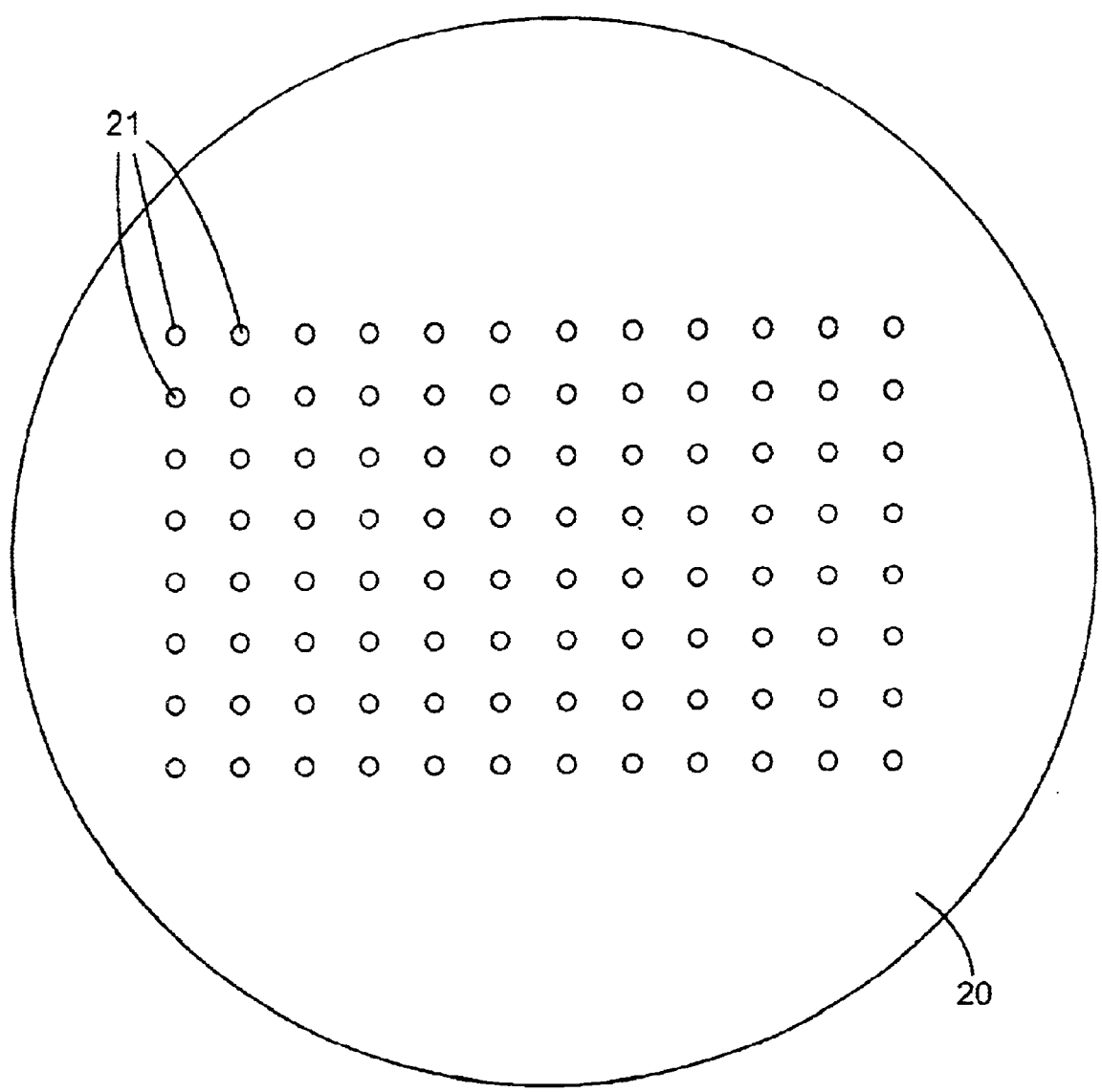
FIG. 2 is a top plan view of a top plate of the present invention.

Referring to FIG. 1, a loading system 10, comprising a first (ie: top) plate 20 and a second (i.e.: bottom) plate 30 is provided. In preferred aspects, plates 20 and 30 are bonded together by a variety of methods including thermal bonding (ideal if both plates are glass in which a low temperature melting point glass layer can be used), gluing (ideal if one or both of the plates are plastic in which a low temperature melting point layer can be used between the plates), or anodic bonding (ideal when bonding a glass plate to a silicon plate).

A sample analysis system, which may preferably comprise an electrophoretic capillary separation microplate 40 is provided under plates 20 and 30. In accordance with the present invention, a plurality of samples (which are placed into each of holes 21 in plate 20) can be simultaneously loaded into sample wells 41 on plate 40 such that the samples can then be simultaneously electrophoretically separated in radially disposed channels 42 (FIG. 4) in microplate 40.

In accordance with the present invention, holes 21 may be disposed in an orthogonal array (for example, an 8 by 12, i.e.: 96 well array) on plate 20 as shown. As will be explained, an advantage of providing wells 21 in an orthogonal array format is that a plurality of different samples (e.g.: 96 different samples) can be easily individually loaded therein, such as by an automated robotic sample loading system or simply by positioning a 96 well microplate thereover, with holes in the bottom of each of the wells permitting the fluid samples to flow through the bottom of the 96 well microplate and into holes 21, positioned in alignment therebelow.

Holes 21 pass fully through plate 20, and may preferably comprise cylindrically shaped apertures which may be microfabricated to pass through plate 20 by processes including drilling with a high speed water-cooled diamond bit, laser drilling, powder blasting, deep-reactive ion etching (DRIE), molding or be manufactured by ultrasound.

Figure 3:
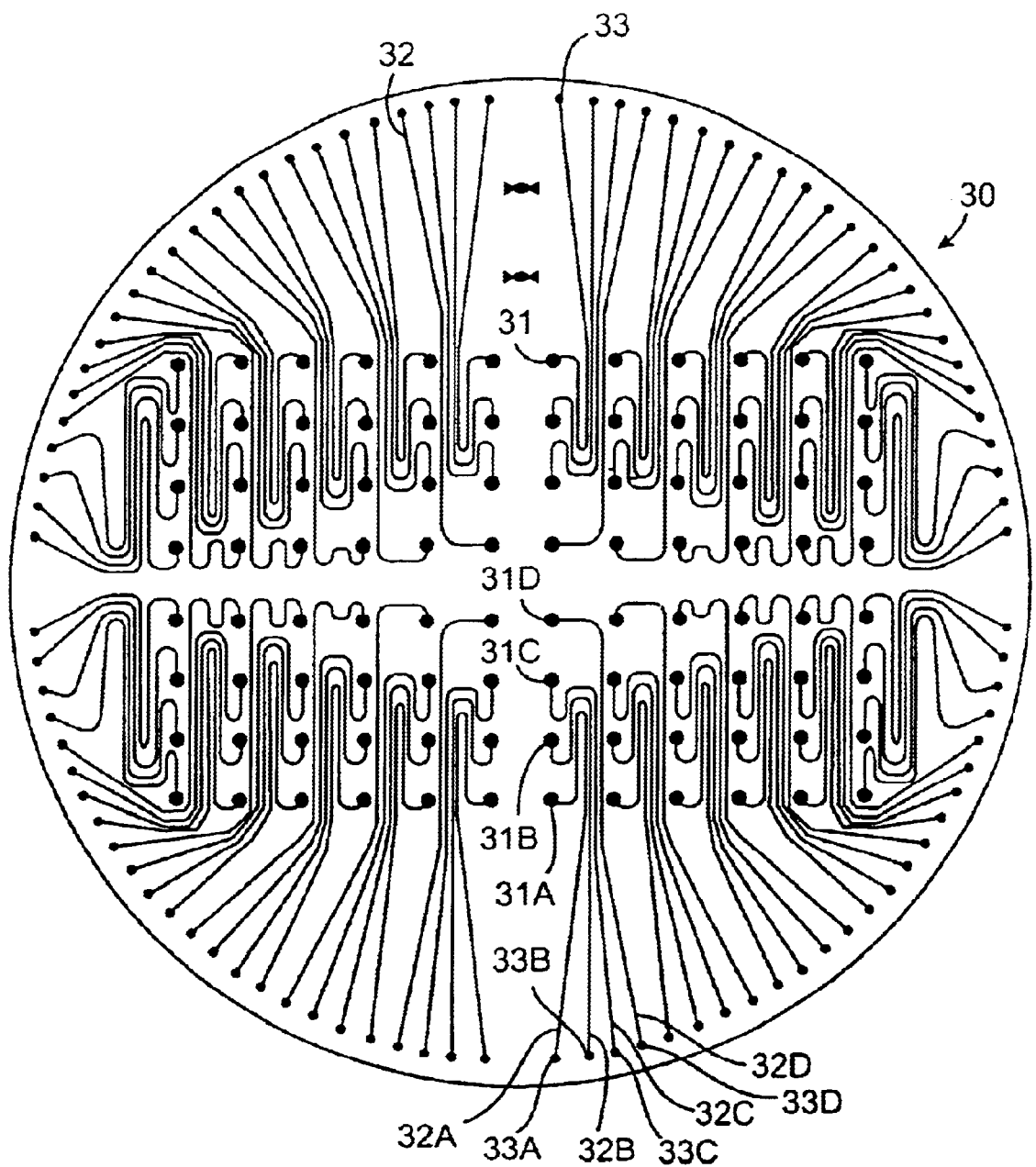
FIG. 3 is a top plan view of a bottom plate of the present invention.

The samples received into holes 21 pass directly into wells 31 (FIG. 3) located therebelow. Referring to FIG. 3, the samples in wells 31 are moved through channels 32 into holes 33, as will be explained. Wells 31 and channels 32 do not pass fully through plate 30, but are instead simply formed (e.g.: etched) across its upper surface. Wells 33 pass fully through plate 30, and may preferably comprise cylindrically shaped apertures which may be microfabricated to pass through plate 30 by processes including drilling with a high speed water-cooled diamond bit, laser drilling, powder blasting, deep-reactive ion etching (DRIE), molding or be manufactured by ultrasound. Channels 32 connect wells 33 to holes 31, as shown. In preferred aspects, microchannels 32 are fabricated to a depth in the range of 5 to 300 um, and most preferably about 10 to 100 um.

In various aspects of the present invention, channels 32 are formed into the top surface of bottom plate 30, as shown. It is to be understood, however, that channels connecting wells 31 with holes 33 may alternatively be formed (e.g.: etched) directly into the bottom surface of top plate 20 (e.g.: see channels 32 FIG. 5A).

In accordance with the present invention, the array of wells on both the dispensing and receiving sides of the wafer stack can be in any desired pattern. Specifically, any array of wells 21 on plate 20 can be connected to any array of wells 33 on plate 30. As such, different plate designs may comprise different numbers of wells/holes therein.

Accordingly, in preferred aspects, the present system can be used to transfer fluid samples from standard 96 well or 384 well microplates into a 96 or 384 channel radial electrophoretic separation microplate.

As can be seen in FIG. 3, each of channels 32A, 32B, 32C and 32D (linking wells 31A, 31B, 31C and 31D with holes 33A, 33B, 33C and 33D, respectively) may preferably have the same length, consequently holding the same sample fluid volume.

This is advantageous such that "uniform" loading can be achieved, with the various samples all being loaded into their individual wells 41 (FIG. 4) at the same time, and with the same fluid volume. An equal volume in each of microchannels 32 can be achieved by adjusting the width or depth of the channels (e.g.: forming wider channel sections or pools mid-way along the channels) as well as adjusting the length of the channels, (e.g.: by providing variously curved or serpentine channels), when microfabricating plate 30.

Figure 4:
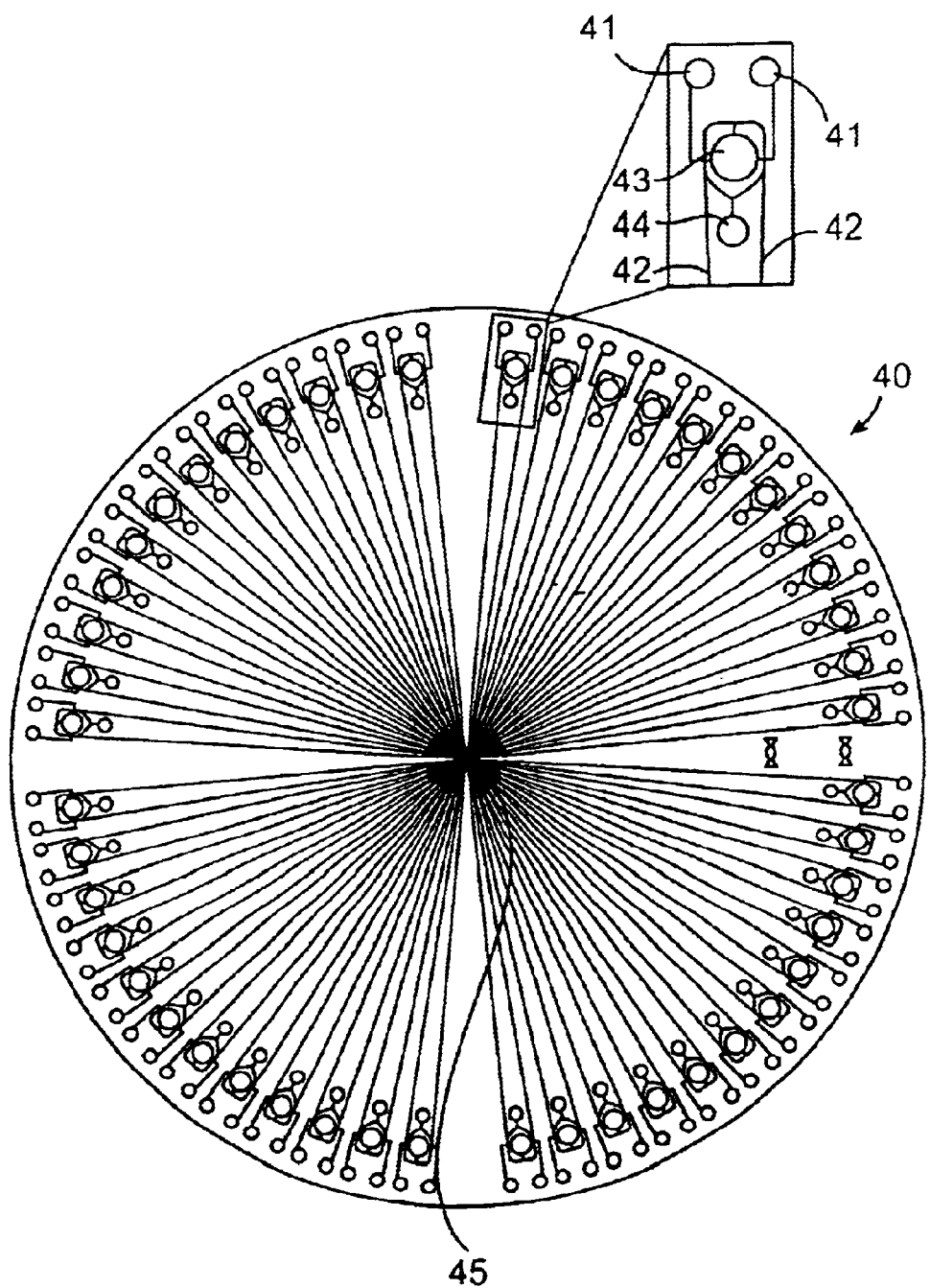
FIG. 4 is a top plan view of a receiving microplate comprising a radial channel microcapillary electrophoresis analysis system.

As can be seen in FIG. 4, electrophoretic separation microplate 40 may optionally comprise sample wells 41, a plurality of separate anodes 43, a plurality of waste reservoirs 44, and a multiplexed centrally positioned cathode 45. Electrophoretic separation can be achieved by first applying a voltage between sample reservoirs 41 and waste reservoir 44 such that plugs of sample are loaded onto each of the separation channels 42. Thereafter, a voltage may be applied between anodes 43 and cathode 44, simultaneously electrophoretically separating each of the samples loaded onto separation channels 42. It is to be understood that the positions of the cathodes and anodes can be reversed such that a plurality of cathodes are disposed around the perimeter of the microplate with a multiplexed centrally positioned anode.

Figure 5A:
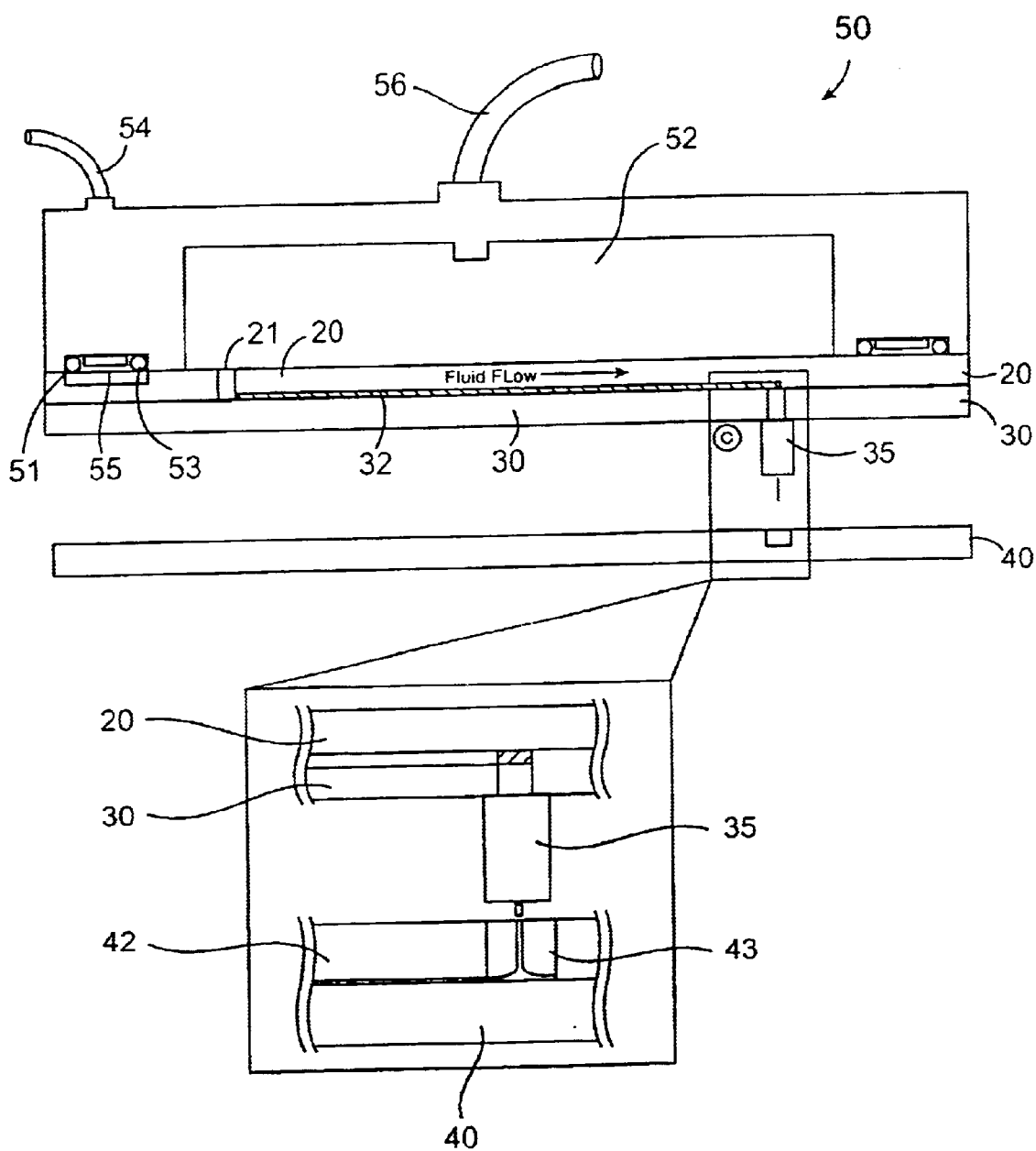
FIG. 5A is a sectional elevation view of the present invention.

Referring to FIG. 5A, the present pressure manifold is illustrated in the sectional view. Specifically, pressure manifold 50 is preferably adapted to cover the top surface of plate 20, optionally being disposed around the perimeter of plate 20, with an outer O-ring 51 and an inner O-ring 53 surrounding a sealed region 55 therebetween, as shown. As air is removed through tube 54, by a vacuum source (not shown), a vacuum will be created in sealed region 55 between outer O-ring 51 and an inner O-ring 53, securing manifold 50 to the top surface of plate 20.

Manifold 50 has a large interior void 52. As air is removed through tube 56, the air pressure in void 52 will drop. Conversely, as air pressure is increased through tube 56, the air pressure in void 52 will increase. In accordance with the present invention, however, the pressure exerted on each of the fluid samples deposited in holes 21 will remain equal to one another.

Consequently, pressure manifold 50 can be used to uniformly load samples deposited into holes 21 in plate 20 into holes 41 in microplate 40. Specifically, air is pumped through tube 56 into void 52, uniformly increasing the pressure over holes 21/wells 31. This pressure pushes the samples from wells 31, along through channels 32, into holes 33, and then downwardly into sample wells 41 in plate 40.

By controlling both the magnitude and duration of the applied pressure with pressure manifold 50, a predetermined amount of the samples can be moved (ie: loaded) into wells 41 in a predetermined time.

Figure 5B:
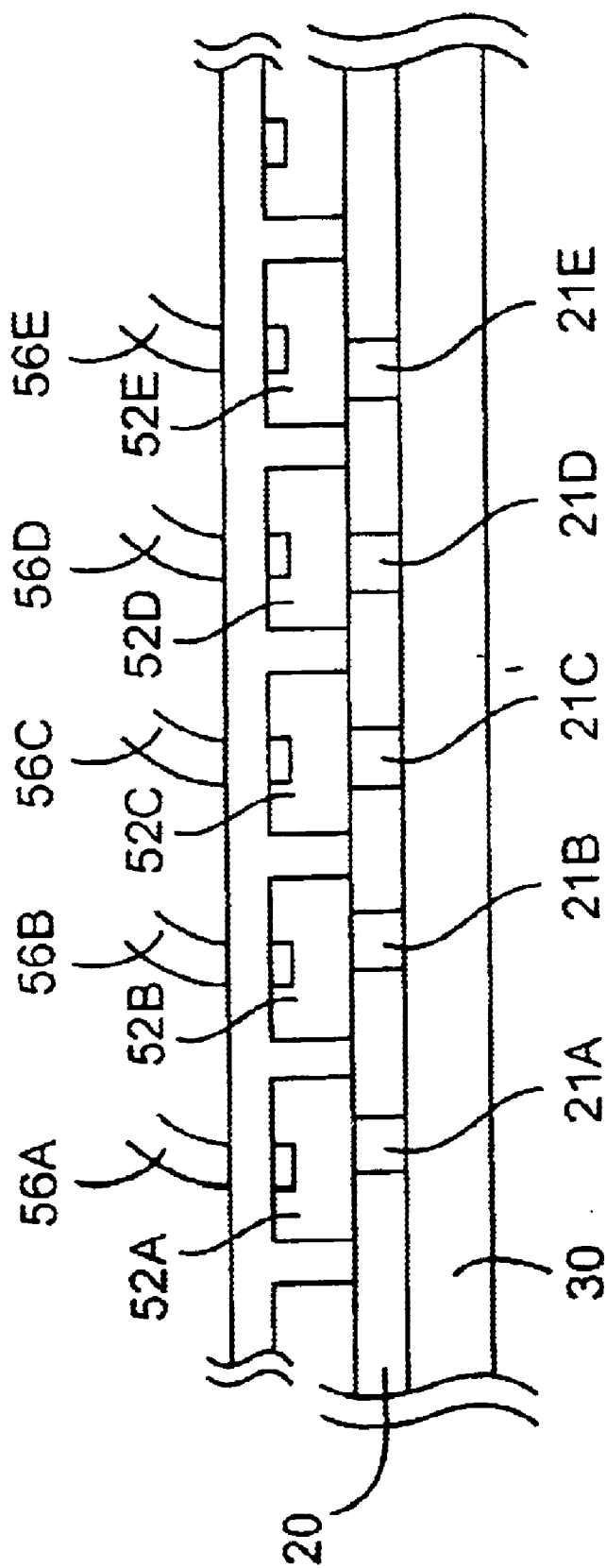
FIG. 5B is a sectional elevation illustration of an alternate aspect of the present invention.

Referring to FIG. 5B, each of individual holes 21A, 21B, 231C, 21D and 21E can have its own dedicated tubes 56A, 56B, 56C, 56D, 56E and 56F, respectively such that holes 21 are individually addressable. Accordingly, fluid samples can be individually directed through loading system 10 and loaded into sample wells 41 in plate 40 at different times, as desired. It is to be understood that holes 21 are preferably disposed in an arcuate path around plate 20, but are shown here in a straight-line path across plate 20 for ease of illustration purposes.

Figure 6A:
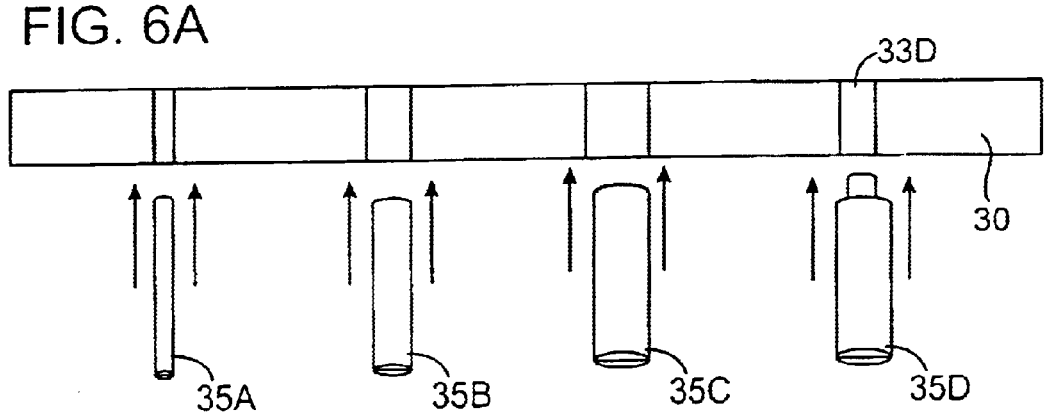
FIG. 6A is an exploded sectional elevation view of a plurality of delivery capillaries placed into the bottom of the bottom plate of the present invention.
Figure 6B:
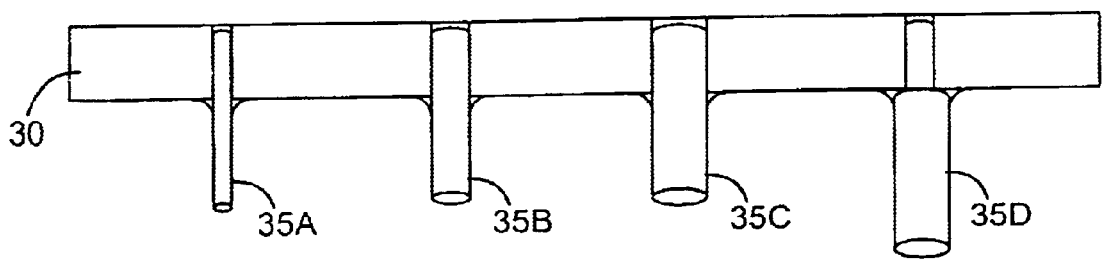
FIG. 6B is an assembled elevation view corresponding to FIG. 6A.
Figure 6C:
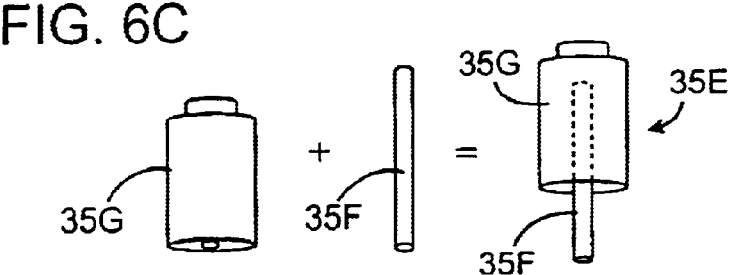
FIG. 6C is a side perspective view of a dual cylinder delivery capillary in accordance with the present invention.

Referring to FIGS. 6A to 6C, delivery capillaries 35, which are received into holes 33 in the bottom side of bottom plate 30 may optionally by provided to load fluid samples directly into wells 41 in receiving microplate 40 therebelow. Delivery capillaries 35 offer the advantages of minimizing dead volume in holes 33 as well as providing a good seal between the capillaries and plate 30. Delivery capillaries 35 may be held in holes 33 by an epoxy or cyanoacrylate adhesive, or be pressure fit into place.

Having a small internal diameter, delivery capillaries 35 have a very small internal volume (e.g.: 5 to 10,000 nL), having internal diameters of about 10 $\mu$m to 100 $\mu$m). Hydrophobic materials such as PEEK and Teflon, hypodermic stainless steel or glass capillaries may be used for forming delivery capillaries 35. An advantage of using hydrophobic materials such as PEEK or Teflon is that they function as a barrier to fluid flow at the end of microchannels 32, which also prevents fluid drops from creeping back up the sides of delivery capillaries 35 during delivery.

To minimize the volume of the capillary which intrudes into the well to be loaded, the ends of the capillaries can optionally be tapered to a point. Alternatively, as shown in FIG. 6C, a compound capillary can be used. Such a compound capillary comprises a length of rigid tubing which is inserted into a larger diameter tube. In particular, a dual tube delivery capillary 35E may be provided, wherein delivery capillary 35E is formed by receiving a first capillary tube 35F into a second capillary tube 35G.

A variety of different diameter delivery capillaries are illustrated in FIGS. 6A and 6B. It is to be understood that each of delivery capillaries 35 selected when fabricating any individual plate 30 are preferably the same. The illustrations of FIGS. 6A and 6B merely show that different designs are possible, ranging from very narrow delivery capillaries 35A through to wider diameter delivery capillaries 35C. Also, delivery capillary 35D shows a design with a collared top upper end which is received into hole 33D. It is also to be understood that delivery capillaries 35 would typically not be disposed in a straight line (as shown in the present sectional view) but would instead be disposed to align with holes 41 in plate 40 (i.e.: in an arcuate path around the outer round perimeter of plate 30), as shown in FIG. 1.

In an optional aspect of the invention, electrical contacts may be disposed in delivery capillaries. For example, first capillary tube 35F in FIG. 6C may be made of stainless steel to accomplish this purpose. Contacts can be made either to the fluids in the microchannels or to thin film contacts microfabricated at the base of each well 41.

In other optional aspects of the invention, a three (or more) layer plate structure is provided. A first additional advantage of using a plurality (i.e.: stack) of separate plates is that the same size wells can be made using larger holes in thin plates, rather than having to machine smaller holes in thicker plates. As such, plate 30 could be replaced by a stack of two or more plates, with these plates each being thinner than plate 30, but having larger diameter wells/holes therein (such that an equal volume of fluid can be contained in an easier to form larger diameter well/hole).

The present layered stack of plates can each be made of glass, silicon or plastics, or other suitable materials. Hybrid structures incorporating layers of different materials are also possible. In addition, hot embossing techniques using silicon or metal master molds can be adapted to the present system.

An additional advantage of adding a third (or more than three) plate layer(s) to the present two plate layer (i.e.: plates 20 and 30) structure is that systems can be provided for one microfluidic channel to pass over another microfluidic channel, without the channels intersecting one another, as follows.

Figure 7D:
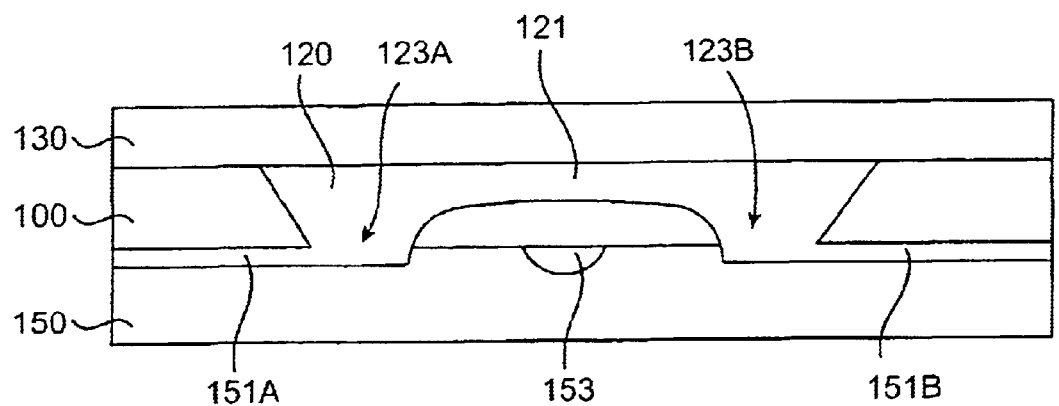
FIG. 7D is a sectional view of the plate of FIG. 7C, with top and bottom plates placed thereabove and therebelow.

Referring to FIGS. 7A to 7D, a third (ie: center) microplate 100 can be differentially etched such that fluid may be transported over a flow channel passing thereunder. Referring to FIGS. 7A and 7B, a photoresist 101 is initially positioned on top of plate 100. As seen from above (FIG. 7A) photoresist 101 may be provided with a "bowtie" shaped hole 103 passing therethrough. After plate 100 has been differentially etched, as shown in FIG. 7C, a recess 120 is etched away, having a center portion 121 (which does not pass through plate 100) and two end portions 123 (which do pass fully through plate 100).

As can be seen in FIG. 7D, photoresist 101 is removed from the top of plate 100 and plate 100 is then be positioned between a top plate 130 and a bottom plate 150. Channels 151A and 151B are disposed (e.g.: etched) along the top surface of plate 150. In addition, a channel 153 (extending in a direction disposed perpendicular to the page) may also be provided. In accordance with this aspect of the invention, a first fluid flow may be directed through channel 151A, passing into the end portion 123A, over center portion 121, and through opposite end portion 123B, and out of opposite channel 151B. A second fluid flow may be directed through flow channel 153 (in a path perpendicular to the page). (Alternatively, channels similar to channels 151 and 153 could instead be formed on the bottom of plate 100 rather than on the top of plate 150).

The differential etching through glass plate 100 can be performed with photolithographically defined masks and hydrofluoric acid etching. Using combinations of small (a few microns wide) and large (tens to hundreds of microns wide) features in the design device, and selection of appropriate photoresist for the masking step, it can be possible to create high aspect ratio etching masks. With thicker resists like AZ 4620 (Clariant-Hoeshst) and SJR 5740 (Shipley), double coatings can result in useful resist thickness up to 25 microns. So, for a small feature such as a 3 micron wide channel masked with a 12 micron coating of photoresist, the aspect ratio becomes 4:1.

An example of etching high-aspect ratio structures is accomplished as follows. Photoresist is first patterned and used as a masking material during the wet chemical etching of glass. The aspect ratio of the masking layer is defined as the photoresist thickness divided by the exposed feature size. Therefore, a feature 5 microns wide which is defined by a 10 micron high layer of photoresist would have an aspect ratio of 2:1 (10/5.)

Accordingly, the differential etching achieved in FIG. 7C is a result of diffusion limited etching in the case of hole 103 with the center of the "bowtie" comprising a narrow channel 104. At channel 104, the aspect ratio of the photoresist layer 101 is very high. This means that there is a "channel" defined on either side by the photoresist masking layer through which the chemical etchant must travel to, and through which the etching products must be removed from. By making this channel very small, the transport of etchant to and products from the surface which is being etched becomes slower than that at the "open" ends of the bowtie.

In accordance with further aspects of the invention, various other multilayer designs are possible, including, but not limited to the following exemplary designs.

Figure 8:
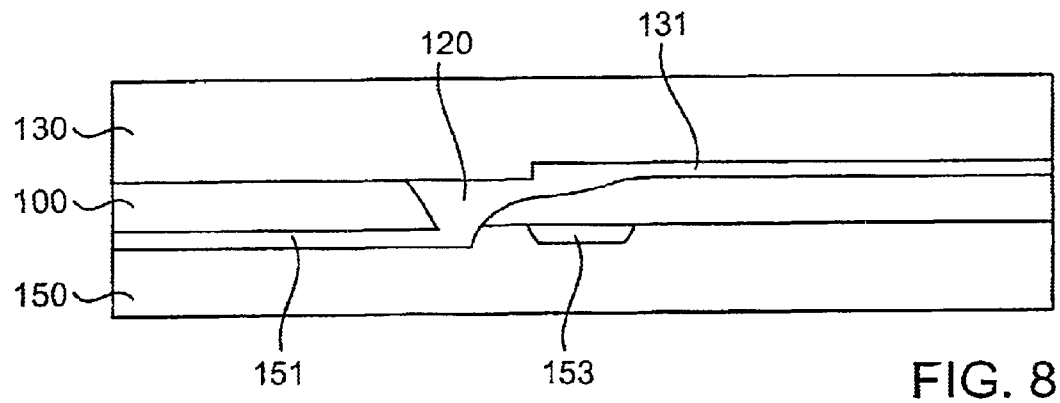
FIG. 8 is a sectional side elevation view of a layered three plate system adapted to shunt fluid from across the top of its bottom layer to across the bottom of its top layer.

As can be seen in FIG. 8, a fluid flow may also be directed through channel 151 (etched onto the top of bottom plate 150) passing through recess 120 into channel 131 (etched into the bottom of top plate 130). A second fluid flow can be directed in a path perpendicular to the page through channel 153 (etched into the top of bottom plate 150).

Figure 9:
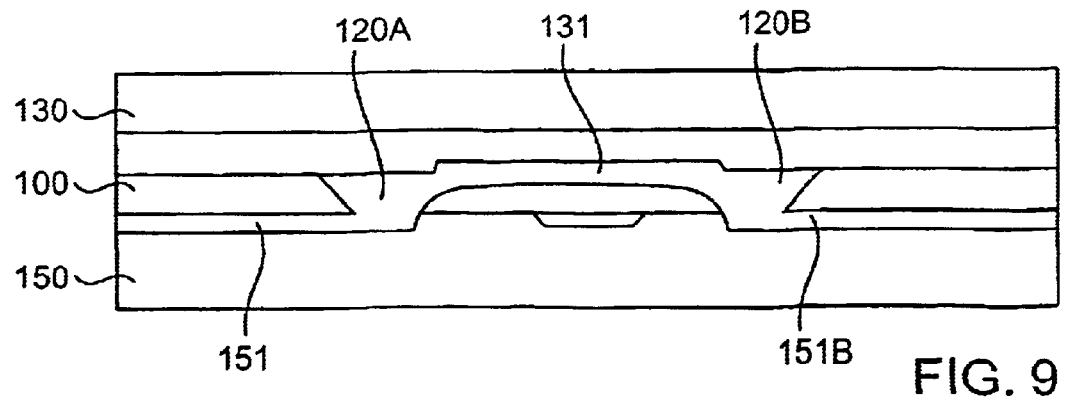
FIG. 9 is a sectional side elevation view of a layered three plate system adapted to shunt fluid from across its bottom layer to across its top layer and then back across to its bottom layer.

As can be seen in FIG. 9, a fluid flow may also be directed through channel 151A (etched onto the top of bottom plate 150) passing through recess 120A into channel 131 (etched into the bottom of top plate 130) and into recess 120B and into channel 151B (etched onto the top of bottom plate 150).

Figure 10:
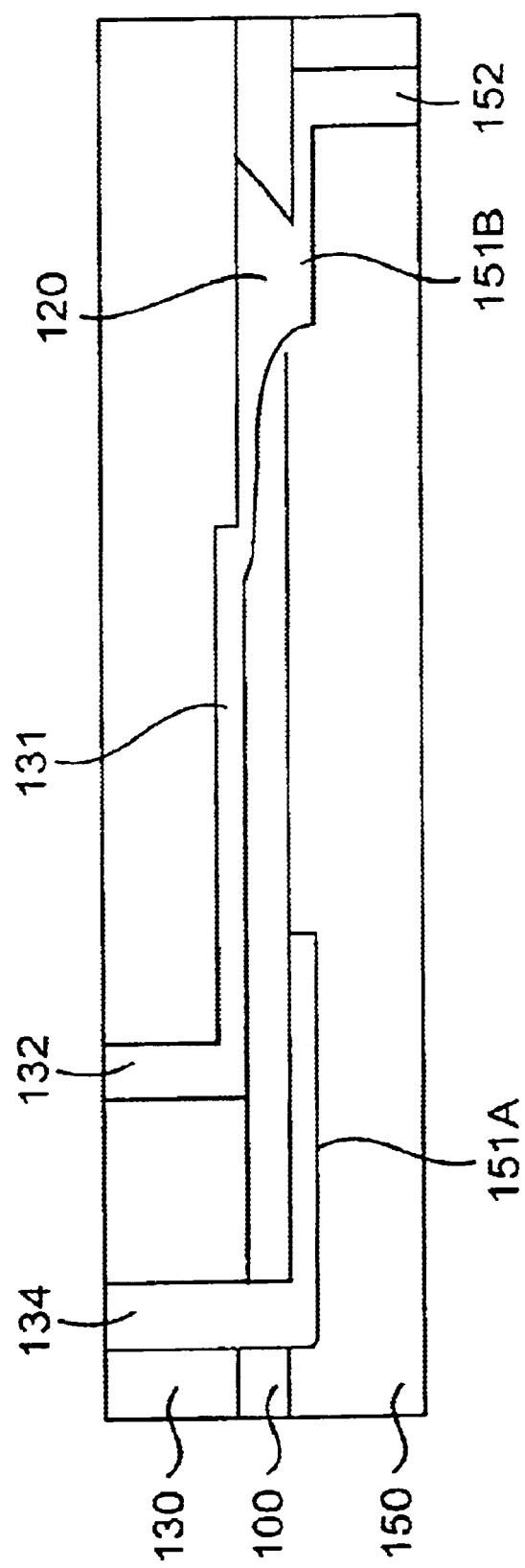
FIG. 10 is a sectional side elevation view of a layered three plate system adapted to shunt fluid in perpendicular directions through microchannels passing above and below one another.

As can be seen in FIG. 10, holes 132 (in top plate 130) and 152 (in bottom plate 150) permit fluid to be passed in a fluid path through the three layer structure (moving through channel 131, recess 120 and channel 151B). A second hole 134 passing through top plate 130 permits fluid to be introduced into channel 151A, (which may permit fluid flow in a path perpendicular to the page).

Figure 11:
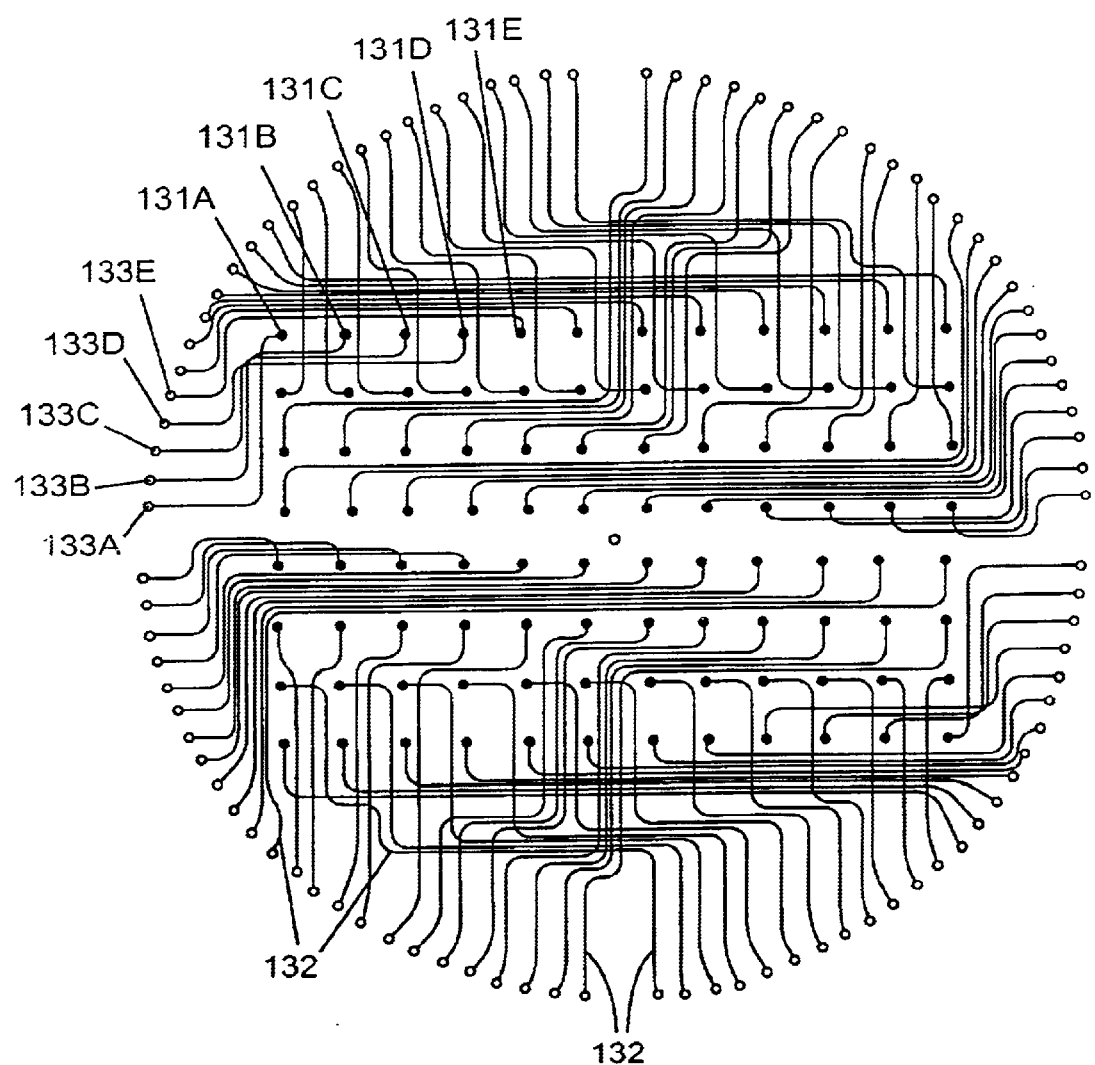
FIG. 11 is a schematic illustration of flow channels passing between a 96 well orthogonal array and a radial well array.

Lastly, FIG. 11 is a schematic illustration of flow channels passing between a 96 well orthogonal array and a radial well array. This design can be achieved with two separate plates (30A and 30B) positioning one on top of another with channels 132 crossing over but not contacting one another (using any of the two-plate channel cross-over designs shown in FIGS. 7D to 10, or any other suitable cross-over design). As can be seen, having channels 132 cross over one another, wells 131A, 131B, 131C, 131D, 131E, etc. can be connected to holes 133A, 133B, 133C, 133D, 133E, etc.

What is claimed is:

1. A microfabricated liquid sample loading system, comprising:

a first plate having an orthogonal array of microfabricated holes passing therethrough;

a second plate positioned against the first plate, the second plate having a geometric array of microfabricated holes passing therethrough, the geometric array of microfabricated holes of the second plate being different from the orthogonal array of microfabricated holes of the first plate; and a plurality of microfabricated channels disposed on a surface of at least one of the first or second plates, the microfabricated channels connecting the orthogonal array of microfabricated holes in the first plate with the geometric array of microfabricated holes in the second plate.

2. The system of claim 1, wherein the microfabricated channels are disposed on the surface of the first plate which is positioned against the second plate.

3. The system of claim 1, wherein the microfabricated channels are disposed on the surface of the second plate which is positioned against the first plate.

4. The microfabricated liquid sample loading system of claim 1, further comprising:

a pressure manifold positioned against the first plate opposite the second plate.

5. The microfabricated liquid sample loading system of claim 4, wherein the manifold is adapted to exert a uniform pneumatic pressure over a surface of the first plate.

6. The microfabricated liquid sample loading system of claim 4, wherein the manifold is adapted to exert different pressures over different holes of the array of microfabricated holes in the 1st plate.

7. The microfabricated liquid sample loading system of claim 4, wherein the manifold comprises a vacuum seal system extending around the perimeter of the first plate, the vacuum seal system securing the manifold to the first plate.

8. The microfabricated liquid sample loading system of claim 1, further comprising:

a plurality of delivery capillaries, each delivery capillary being received within one of the holes passing through the second plate.

9. The system of claim 8, wherein the plurality of delivery capillaries each extend downwardly from the bottom surface of the second plate.

10. The system of claim 8, wherein the plurality of delivery capillaries comprise cylinders received into the holes passing through the second plate.

11. The system of claim 10, wherein the cylinders are made from at least one of the group of materials consisting of PEEK, Teflon, stainless steel and glass.

12. The system of claim 8, wherein the plurality of delivery capillaries comprise first cylinders received into the holes passing through the second plate and second cylinders received into the first cylinders.

13. The system of claim 8, wherein the plurality of delivery capillaries have a tapered lower end.

14. The system of claim 8, wherein the plurality of delivery capillaries have a collared upper end.

15. The system of claim 8, wherein the plurality of delivery capillaries have electrical contacts received therein.

16. The system of claim 1, wherein the volumes of the plurality of microfabricated channels are equal.

17. The system of claim 1, wherein the microfabricated channels have depths of about 5 to 200 um.

18. The system of claim 1, wherein the microfabricated channels have depths of about 10 to 100 um.

19. The system of claim 1, wherein the first and second plates are bonded together by at least one of the group consisting of thermal bonding, gluing, adhesive bonding and anodic bonding.

20. The system of claim 1, wherein the first and second plates are made of at least one of the group consisting of glass, silicon and plastics.

21. The system of claim 1, wherein the array of microfabricated holes passing through the second plate are disposed in a radial array.

22. The system of claim 1, further comprising:
a receiving microplate positioned under the second plate, the receiving microplate having an array of wells positioned in alignment with the holes passing through the second plate.

23. The system of claim 22, wherein the receiving microplate comprises an electrophoretic analysis system.

24. The system of claim 23, wherein the electrophoretic analysis system comprises a plurality of radially disposed electrophoretic separation channels.

25. The system of claim 1, further comprising:
a third plate positioned against the second plate, the third plate having an array of microfabricated holes passing therethrough; and
a plurality of microfabricated channels disposed on a surface of at least one of the first, second or third plates, the microfabricated channels connecting the array of microfabricated holes in the second plate with the array of microfabricated holes in the third plate.

26. The system of claim 25, wherein the holes in the second plate comprise a portion passing fully through the second plate and a portion passing partially through the second plate.

27. The system of claim 26, wherein the holes in the third plate comprise portions passing fully through the third plate and a portion passing partially through the third plate.

28. The system of claim 27, wherein the portions passing fully through the third plate are disposed on opposite sides of the portion passing partially through the second plate.

29. The system of claim 25, wherein the plurality of microfabricated channels disposed on a surface of at least one of the first or second plates cross over, but do not intersect the plurality of microfabricated channels disposed on a surface of at least one of the second or third plates.

30. The system of claim 25, wherein the microfabricated channels comprise:
a first microfabricated channel on the bottom of the first plate or top of the second plate; and
a second microfabricated channel on the bottom of the second plate or the top of the third plate.

31. A method of loading a plurality of samples into a receiving microplate having an array of wells therein, comprising:
providing a microfabricated liquid sample loading system comprising a first plate having an array of microfabricated holes passing therethrough, and a second plate positioned against the first plate, the second plate having an array of microfabricated holes passing therethrough, and a plurality of microfabricated channels disposed on a surface of at least one of the first or second plates, the microfabricated channels connecting the array of microfabricated holes in the first plate with the array of microfabricated holes in the second plate;
providing a receiving microplate having a plurality of wells disposed in alignment with the array of holes passing through the second plate;
depositing the plurality of samples into the array of microfabricated holes passing through the first plate, which includes depositing the plurality of samples in sequence by independently addressing a plurality of the microfabricated holes passing through the first plate;
applying pressure to the array of microfabricated holes in the array of microfabricated holes in the first plate, thereby moving the samples through the microfabricated channels into the array of holes in the second plate and into the wells in the receiving plate.

32. The method of claim 31, wherein depositing the plurality of samples into the array of microfabricated holes passing through a first plate comprises:
depositing the plurality of samples simultaneously by applying a uniform pressure across the top of the first plate.

33. The method of claim 31, wherein applying a pressure to the top of the first plate comprises:
positioning a pressure manifold against the first plate opposite the second plate; and
exerting a uniform pneumatic pressure over a surface of the first plate.

34. The method of claim 33, wherein positioning a pressure manifold against the first plate opposite the second plate comprises:
forming a vacuum seal around the perimeter of the surface of the first plate between the pressure manifold and the surface of the first plate.

35. The method of claim 31, wherein moving the samples from the array of holes in the second plate and into the wells in the receiving plate comprises
passing the samples through delivery capillaries, each delivery capillary being received within one of the holes passing through the second plate.

36. The method of claim 31, further comprising:
electrophoretically separating the samples in channels extending from the wells in the receiving microplate.

37. The method of claim 31, further comprising:
providing a third plate positioned against the second plate, the third plate having an array of microfabricated holes passing therethrough, and a plurality of microfabricated channels disposed on a surface of at least one of the second or third plates, the microfabricated channels connecting the array of microfabricated holes in the second plate with the array of microfabricated holes in the third plate, and wherein the holes in the second plate comprise a portion passing fully through the second plate and a portion passing partially through the second plate, wherein the a plurality of microfabricated channels disposed on a surface of at least one of the first or second plates cross over, but do not intersect the plurality of microfabricated channels disposed on a surface of at least one of the second or third plates.

38. A method of transferring small volumes of liquid sample, the step comprising;
providing an orthogonal array of sample wells containing the small volumes of liquid sample; and transferring a liquid sample in the sub-microliter range from the orthogonal array of sample wells to a different geometric array of sample wells through microfluidic channels, wherein microfluidic channels are etched into sandwiched glass surface structures.

39. A microfabricated liquid sample loading system, comprising;
   a first glass wafer structure having an orthogonal array of sample wells;
   a second glass wafer structure facing the first glass wafer structure and having a geometric array of sample wells which are different from the orthogonal array of sample wells of the first glass wafer structure; and
   a plurality of microfluidic channels etched into at least one of the first and second glass wafer structure, the microfluidic channels connecting the orthogonal array of sample wells of the first glass wafer structure with the geometric array of sample wells of the second glass wafer structure.

40. The microfabricated liquid sample loading system of claim 39 wherein the geometric array of microfabricated holes of the second plate are disposed in a radial array.

41. The microfabricated liquid sample loading system of claim 39 wherein the plurality of microfluidic channels are etched into sandwiched glass surface structures formed between the first glass wafer structure and the second glass wafer structure.

* * * * *

UNITED STATES PATENT AND TRADEMARK OFFICE
CERTIFICATE OF CORRECTION

PATENT NO.   : 6,623,613 B1
DATED        : September 23, 2003
INVENTOR(S)  : Mathies et al.

It is certified that error appears in the above-identified patent and that said Letters Patent is hereby corrected as shown below:

Drawings,
Figure 9, channel "151" should be -- 151A --

Column 5,
Line 40, "231C" should be -- 21C --

Signed and Sealed this

Thirtieth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,623,613 B1 Page 1 of 1
APPLICATION NO. : 09/678351
DATED : September 23, 2003
INVENTOR(S) : Richard A. Mathies et al.

It is certified that error appears in the above-identified patent and that said Letters Patent is hereby corrected as shown below:

At Column 1, Line 10, please insert the following:

-- GOVERNMENT RIGHTS NOTICE

The Invention was made with support from the U.S. Government under Grant No. HG01399 awarded by the National Institute of Health. The U.S. Government has certain rights in the invention. --

Signed and Sealed this

Twenty-first Day of April, 2009

JOHN DOLL
*Acting Director of the United States Patent and Trademark Office*